United States Patent
Bhagchandani et al.

(10) Patent No.: US 9,586,032 B2
(45) Date of Patent: Mar. 7, 2017

(54) VARIABLE LENGTH BALLOON

(71) Applicant: Cook Incorporated, Blomington, IN (US)

(72) Inventors: Neha Bhagchandani, Newport Beach, CA (US); Alyson M. Tews, Bloomington, IN (US); Elizabeth M. Theobald, Bloomington, IN (US); Alina Costin, Bloomington, IN (US); Christopher Michael Mobley, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 153 days.

(21) Appl. No.: 14/207,299

(22) Filed: Mar. 12, 2014

(65) Prior Publication Data

US 2014/0277069 A1    Sep. 18, 2014

Related U.S. Application Data

(60) Provisional application No. 61/777,129, filed on Mar. 12, 2013.

(51) Int. Cl.
*A61M 29/00* (2006.01)
*A61M 25/10* (2013.01)

(52) U.S. Cl.
CPC ...... *A61M 25/104* (2013.01); *A61M 25/1027* (2013.01); *A61M 2025/1031* (2013.01); *A61M 2025/1059* (2013.01); *A61M 2025/1068* (2013.01)

(58) Field of Classification Search
CPC ............ A61M 25/104; A61M 25/1027; A61M 2025/1031; A61M 2025/1059; A61M 2025/1068; A61M 2025/1072; A61M 25/1018; A61M 25/10187; A61M 25/1038; A61M 2025/1065; A61M 2025/1081; A61M 2025/1084
See application file for complete search history.

(56) References Cited

U.S. PATENT DOCUMENTS

| | | |
|---|---|---|
| 5,270,086 A * | 12/1993 | Hamlin ................. A61L 29/041 428/35.2 |
| 5,304,135 A | 4/1994 | Shonk |
| 5,415,635 A | 5/1995 | Bagaoisan et al. |
| 5,961,536 A | 10/1999 | Mickley et al. |

(Continued)

OTHER PUBLICATIONS

About. Dictionary.com. Dictionary.com Unabridged. Random House, Inc. http://www.dictionary.com/browse/about (accessed: Jun. 12, 2016).*

*Primary Examiner* — Jonathan Miles
*Assistant Examiner* — Kankindi Rwego
(74) *Attorney, Agent, or Firm* — Brinks Gilson & Lione; John C. Bacoch

(57) ABSTRACT

A variable length balloon catheter assembly and methods for inflating a variable length balloon to a predetermined length. The variable length balloon catheter has a balloon at a distal end and a plurality of stricture mechanisms securing the balloon to the catheter. The stricture mechanisms are provided at known intervals and have a known rupture pressure. The balloon is inflated and a known number of stricture mechanisms are ruptured providing for a variable balloon length based on the number of stricture mechanisms ruptured.

14 Claims, 3 Drawing Sheets

(56) References Cited

U.S. PATENT DOCUMENTS

| | | | |
|---|---|---|---|
| 6,527,741 B1 | 3/2003 | Lee et al. | |
| 6,796,960 B2 * | 9/2004 | Cioanta | A61B 18/04 604/103.01 |
| 6,884,257 B1 | 4/2005 | Cox | |
| 7,198,632 B2 | 4/2007 | Lim et al. | |
| 7,402,168 B2 * | 7/2008 | Sanderson | A61F 2/915 604/101.01 |
| 2003/0135266 A1 * | 7/2003 | Chew | A61F 2/915 623/1.16 |
| 2007/0073328 A1 * | 3/2007 | Kennedy, II | A61M 25/10 606/192 |
| 2012/0277718 A1 | 11/2012 | Campbell et al. | |

\* cited by examiner

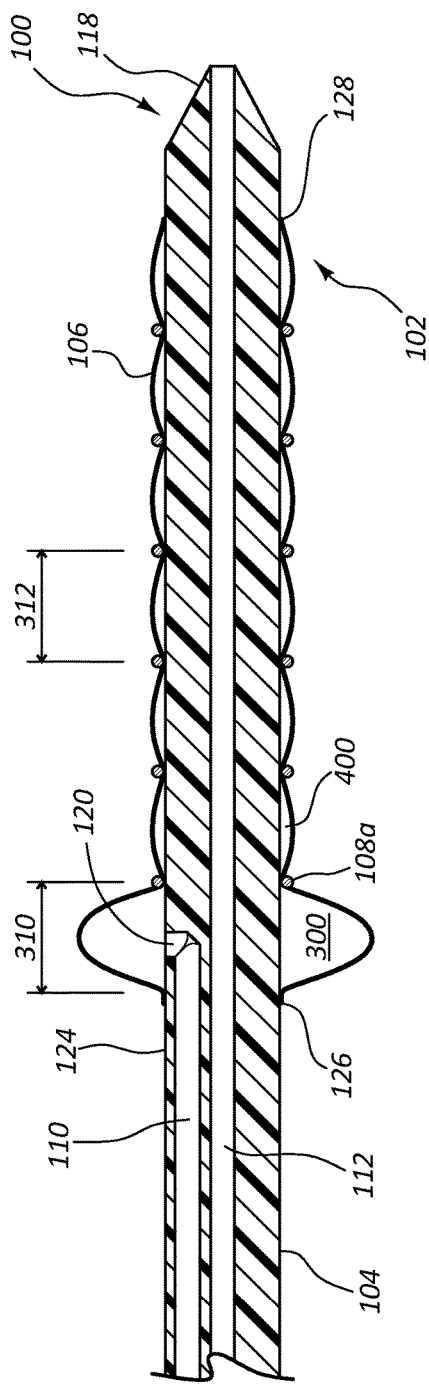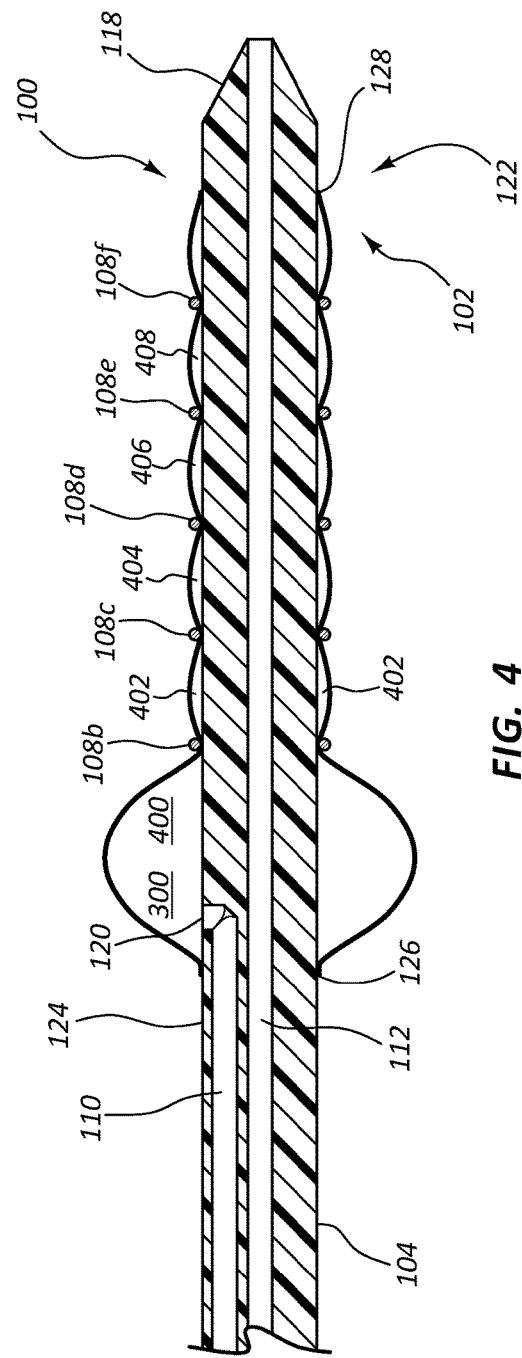

VARIABLE LENGTH BALLOON

RELATED APPLICATIONS

The present patent document claims the benefit of the filing date under 35 U.S.C. §119(e) of Provisional U.S. Patent Application Ser. No. 61/777,129 filed Mar. 12, 2013, which is hereby incorporated by reference.

FIELD

Embodiments of the present invention relate to a variable length balloon and to methods for controlling the length of an inflated balloon.

BACKGROUND

Critical limb ischemia (CLI) is a severe blockage in the arteries which significantly reduces blood flow. CLI is a serious form of peripheral arterial disease and is caused by atherosclerosis, the hardening, and narrowing of the arteries due to the buildup of plaque. One of the treatment options for CLI is balloon angioplasty. For this procedure the surgeon can gain access through the femoral or the tibiopedal arteries using common surgical techniques such as the Seldinger technique. In these patients tibiopedal access is easier than femoral access since the amount of calcification of the arteries is higher on the femoral side.

Because the vessel is blocked by the buildup of plaque, it is necessary to carry out the balloon angioplasty in the arterial wall due to limited access available in the blocked arterial lumen. A wire guide is passed through the arterial wall and the balloon angioplasty is performed to open up the vessel wall. Due to access gained only from one side of the blockage, it is difficult to estimate the length of the balloon needed for the angioplasty of the arterial wall.

Currently, the angioplasty procedure is performed by gaining access into wall of the occluded artery and using a wire guide to move to the other end of the calcification. This is usually done by passing a wire guide or a stiff ended catheter through the arterial wall. Once access is gained though the calcification contrast injection is carried out to size the occlusion and then the balloon with the required size is used to carry out the angioplasty.

It would be beneficial to have a balloon catheter having a variable length balloon rather than having to select a balloon size after sizing the occlusion. It would be helpful if the length of the balloon could be varied during a procedure.

SUMMARY

In one embodiment a balloon catheter assembly comprises a catheter, a variable length balloon, a first stricture mechanism, and a second stricture mechanism. The catheter has a distal end, a proximal end, and a lumen extending from the proximal end to the distal end. The variable length balloon is disposed on the distal end of the catheter and has an inner volume in fluid communication with the lumen. The inner volume is defined by an outer surface of the catheter and an inner surface of a balloon wall. The first pressure dependent stricture mechanism constricts a first circumferential portion of the balloon wall proximate the outer surface of the catheter and has a first pre-determined rupture pressure. The second pressure dependent stricture mechanism constricts a second circumferential portion of the balloon wall proximate the outer surface of the catheter and has a second pre-determined rupture pressure. The first pressure dependent stricture mechanism and the second pressure dependent stricture mechanism divide the inner volume into longitudinal sections.

Another embodiment is directed to a method for varying the length of a balloon on a balloon catheter. The balloon catheter has a balloon wall enclosing an inner volume and a first plurality of stricture mechanism dividing the balloon into uniform lengths with each stricture mechanism having a predetermined rupture pressure threshold. The method comprises guiding the balloon to an inflation location, determining a desired length to inflate the balloon, determining a second plurality of stricture mechanism to rupture to achieve a working length near the desired length the balloon, for each of the plurality of stricture mechanisms, rupturing the stricture mechanism by introducing fluid into the inner volume of the balloon sufficient to exceed the rupture pressure threshold of the stricture mechanisms, and introducing fluid to expand the balloon at a pressure less than a predetermined rupture pressure threshold of a stricture mechanism not among the second plurality of stricture mechanisms.

Another embodiment is directed to a method of manufacturing a variable length catheter assembly. The method comprises obtaining a catheter having at least one inflation lumen and an inflation port in fluid communication with the inflation lumen, placing a balloon material about an outer surface of the catheter at a distal end of the catheter, securing the balloon material in a circumferential strip to the outer surface of the catheter proximal to the inflation port, securing the balloon material in a circumferential strip to the outer surface of the catheter distal to the inflation port, and attaching a plurality of pressure dependent stricture mechanisms in circumferential strips about the catheter. The plurality of pressure dependent stricture mechanisms form a pressure dependent attachment of the circumferential strip of the balloon material to the outer surface of the catheter.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which:

FIG. 3 illustrates the cross-sectional view of FIG. 2 with a balloon section expanded.

FIG. 4 illustrates the cross-sectional view of FIG. 2 with two balloon section expanded.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

In the following discussion, the terms "distal" and "proximal" will be used to describe the opposing axial ends of the inventive balloon catheter, as well as the axial ends of various component features. The term "distal" is used in its conventional sense to refer to the end of the apparatus (or component thereof) that is furthest from the operator during use of the apparatus. The term "proximal" is used in its conventional sense to refer to the end of the apparatus (or component thereof) that is closest to the operator during use. For example, a catheter may have a distal end and a proximal end, with the proximal end designating the end closest to the operator heart during an operation, such as a handle, and the distal end designating an opposite end of the catheter, such as treatment tip. Similarly, the term "distally" refers to a direction that is generally away from the operator along the apparatus during use and the term "proximally" refers to a direction that is generally toward the operator along the apparatus.

Figure 1:
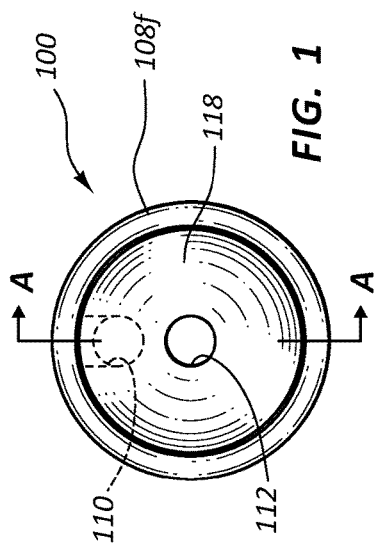
FIG. 1 illustrates a head on view of the distal end of a variable length catheter.
Figure 2:
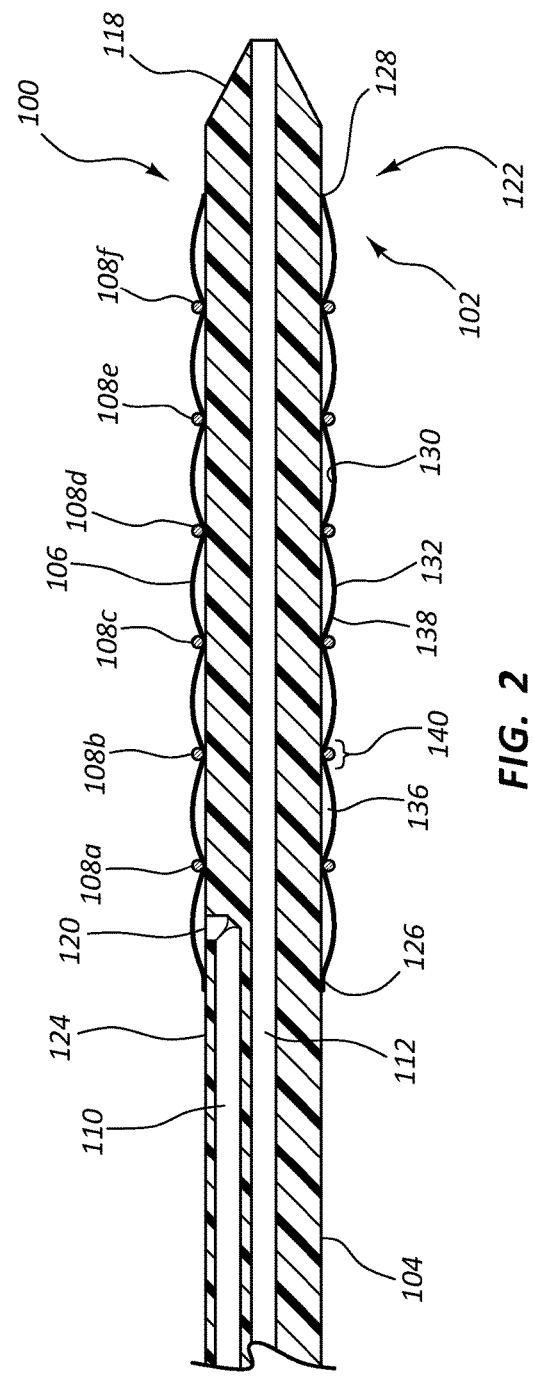
FIG. 2 illustrates cross-sectional view A-A of the distal end of variable length balloon catheter of FIG. 1.

FIG. 1 illustrates the distal end 102 of a variable length balloon catheter assembly 100 head on. FIG. 2 illustrates a cross-section of the variable length balloon catheter assembly 100 of FIG. 1 taken along section AA. The variable length balloon catheter assembly 100 is comprised of a catheter 104, a variable length balloon 106, and a plurality of pressure dependent stricture mechanisms 108.

The catheter 104 has a distal end 122 and a proximal end (not shown). An inflation lumen 110 runs distally from an inflation source towards the variable length balloon 106. An inflation port 120 provides fluid communication between the inflation lumen 110 and an outer surface 124 of the catheter 104. In some embodiments, the catheter 104 may include a second lumen 112 that extends to the distal end 122 of the catheter 104. The second lumen may be configured for the passage of a wire guide or contrast fluid there through. The catheter 104 may have a conical tip 118 that facilitates pushing the distal end 122 of the catheter 104 past an occlusion.

The variable length balloon 106 is disposed about a distal portion of the catheter 104 and covers the inflation port 120. The variable length balloon 106 is secured at its proximal end 126 to the catheter outer surface 124 proximal to the inflation port 120 and is secured at its distal end 128 distal to the inflation port 120. An inner volume 136 is formed between an inner surface 130 of the variable length balloon 106 and the outer surface 124 of the catheter 104. The variable length balloon 106 may have a wall 132 comprised of an elastic material such that an increase in fluid pressure within the inner volume 136 will cause the variable length balloon 106 to inflate, stretching the wall 132. In other embodiments the wall 132 may be comprised of a relatively inelastic material and the wall 132 is folded, compacting the variable length balloon 106 about the catheter 104. An increase in fluid pressure within the inner volume 136 will cause the variable length balloon 106 to expand, unfolding the wall 132.

The plurality of stricture mechanisms 108 divide the inner volume 136 into at least three sub volumes, each sub volume being substantially sealed from one another. The stricture mechanisms 108 are pressure sensitive, such that when a fluid pressure is exceeded in a sub volume immediately adjacent to the stricture mechanism 108, the stricture mechanism 108 fails allowing fluid communication between the sub volumes immediately adjacent to the stricture mechanism 108. In the embodiment of FIG. 2, the stricture mechanism 108 comprises a suture wrapped circumferentially about an outer surface 138 of the variable length balloon 106. The suture holds a narrow circumferential segment 140 of the inner surface 130 of the wall 132 against the outer surface 124 of the catheter 104, such that fluid flow between the sub volumes immediately adjacent the suture is inhibited. Additional sutures further divide the inner volume 136 of the variable length balloon 106. Each of the sutures is calibrated to fail at predetermined pressure. The pressure at which the suture fails can be adjusted using commonly known techniques such as varying the size of the suture and/or changing the composition of the suture. For example, the pressure at which a round suture fails can be increased by using a larger diameter suture or switching to a suture having a higher tensile strength. The suture may be comprised of a bioadsorbable material such that it may be left in the body of a patient if it is detached from the variable length balloon catheter assembly 100 during use.

In some embodiments each of the sutures may have the same predetermined failure pressure. In other embodiments each of the sutures may have a different failure pressure that gradually increases in a distal direction. For example, a suture 108a immediately adjacent the port 120 may have a failure pressure of 15 pounds per square inch (psi.) while the next suture 108b may have a failure pressure of 20 psi. The next suture 108c may have a failure pressure of 25 psi and so on. These values are merely exemplary and embodiments of the invention are not limited to these pressures.

Each of the sutures may be disposed at regular intervals along the outer surface 124 of the catheter 104. For example, each suture may be disposed 2 centimeters (cm.) from each adjacent suture. In other embodiments the sutures may be placed at irregular intervals. Thus the length that the variable length balloon 106 extends as it is inflated is determined depending on the number of sutures that have failed. In the embodiment in which the suture are spaced at regular intervals, the inflated length may be found by multiplying the distance between sutures times the number of sutures that failed and adding the result to the initial balloon length. In embodiments in which the spacing is irregular, the inflated length may be found by totaling the spacing after each failed suture and adding the total to the initial balloon length.

While the present embodiment has been described in terms of sutures, other stricture mechanisms 108 may be used. Generally, any mechanism that prevents a circumferential portion of the variable length balloon 106 from expanding and that fails at a predetermined pressure may be used as a stricture mechanism 108.

In some embodiments the stricture mechanism 108 may be an adhesive applied in a circumferential strip between the inner surface 130 of the balloon 106 and the outer surface 124 of the catheter 104. In these embodiments the adhesive inhibits fluid from flowing between adjacent sub volumes. The adhesive will continue to inhibit the fluid flow until the predetermined pressure is reached, at which time the adhesive fails. The failure of the adhesive allows the variable length balloon 106 to expand where the adhesive was applied allowing fluid to flow between adjacent sub volumes and further inflating the variable length balloon 106. The predetermined failure pressure can be adjusted using techniques known in the art such as varying the width of the adhesive circumferential strip and/or using different glue formulations.

In another embodiment, the variable length balloon 106 may be made of multiple layers of material having different melting points. For example the variable length balloon 106 may be coextruded with the inner layer having a lower melting point than the outer layer. During manufacturing, circumferential strips of the variable length balloon may be bonded to the catheter at a temperature sufficient to bond the inner layer while maintaining the structure and form of the outer layer. The bonded circumferential strip would be the stricture mechanism and would release at a predetermined pressure within the variable length balloon. The pressure at which the bonded circumferential strip is released may be varied using techniques such as changing the width of the bonded circumferential strip or changing the temperature at which the circumferential strip is bonded.

FIG. 3 illustrates the variable length balloon catheter assembly 100 of FIG. 2 in the process of being inflated to a known length. In practice the distal end 102 of the variable length balloon catheter assembly 100 will first be guided to a treatment location. In some embodiments, a guidewire is guided to a treatment location and is passed through an arterial wall to bypass an occlusion. The distal end 102 of the variable length balloon catheter assembly 100 is then delivered over the guidewire using the second lumen 112 until the proximal end 126 of the variable length balloon 106 is proximate the occlusion. The user may then determine a desired length of the variable length balloon 106 using commonly available techniques, such as contrast dye injection or a simple estimate of the occlusion size.

Once the desired length of the variable length balloon 106 has been determined, the user then makes a determination as to the number of stricture mechanisms 108 to rupture to obtain a working length near the desired length. The working length of the variable length balloon 106 is dependent upon the number of stricture mechanisms 108 ruptured and the spacing 312 between each stricture mechanism 108. In some embodiments the user may use a working length that is the minimum length that is greater than the desired length, or in other embodiments the working length may be the length nearest to the desired length.

An example of determining the number of stricture mechanisms 108 to rupture will now be given. For purposes of this example, an exemplary variable length balloon 106 having a having a spacing of 2 cm. between adjacent stricture mechanisms 108 and an initial balloon length 310 of 2 cm will be used. If it is determined that the desired length is 10.5 cm. long, the number of stricture mechanisms 108 to rupture can be found by subtracting the initial balloon length 310, and dividing the result (8.5 cm) by the spacing 312 between stricture mechanisms 108 (2 cm.) which results in 4.25 stricture mechanisms 108 to rupture. Since the stricture mechanisms 108 are a discreet quantity, it is necessary to select either 4 or 5 stricture mechanisms 108. In some embodiments, it may be desirable that the balloon extend at least the desired length. In such embodiments it would be necessary to rupture 5 stricture mechanisms 108 resulting in a balloon length of 5*2 cm+2 cm for a working balloon length of 12 cm. In other embodiment it may be desirable that the working length of the balloon be as close to the desired length as possible. In such cases it would be necessary to rupture 4 stricture mechanism 108 for a balloon length of 4*2 cm+2 cm=10 cm.

Once the number of stricture mechanisms 108 to rupture is determined, the user inflates the first sub volume 300 of the variable length balloon 106 in fluid communication with the port 120 as shown in FIG. 3. In FIG. 3 the first sub volume 300 of the balloon 106 is shown being inflated with the remaining sub volumes being uninflated. Stricture mechanism 108a prevents the balloon 106 from expanding beyond the first sub volume 300 until a first predetermined rupture pressure is reached.

FIG. 4 illustrates the variable length balloon catheter 100 of FIG. 2 with the first stricture mechanism 108a being ruptured. The first sub volume 300 and the second sub volume 400 are now in fluid communication and both inflate as the inflation fluid enters the combined sub volumes. The pressure within the combined sub volumes increases until reaching the predetermined rupture pressure of the second stricture mechanism 108b at which point the second stricture mechanism 108b ruptures enabling fluid communication between the combined sub volumes and the third sub volume 402. This process is repeated until the desired number of stricture mechanisms 108 are ruptured. Once the desired number of stricture mechanisms 108 have been ruptured, the variable length balloon 106 may be inflated to a working pressure less than the next rupture pressure of the next stricture mechanism 108.

Figure 5:
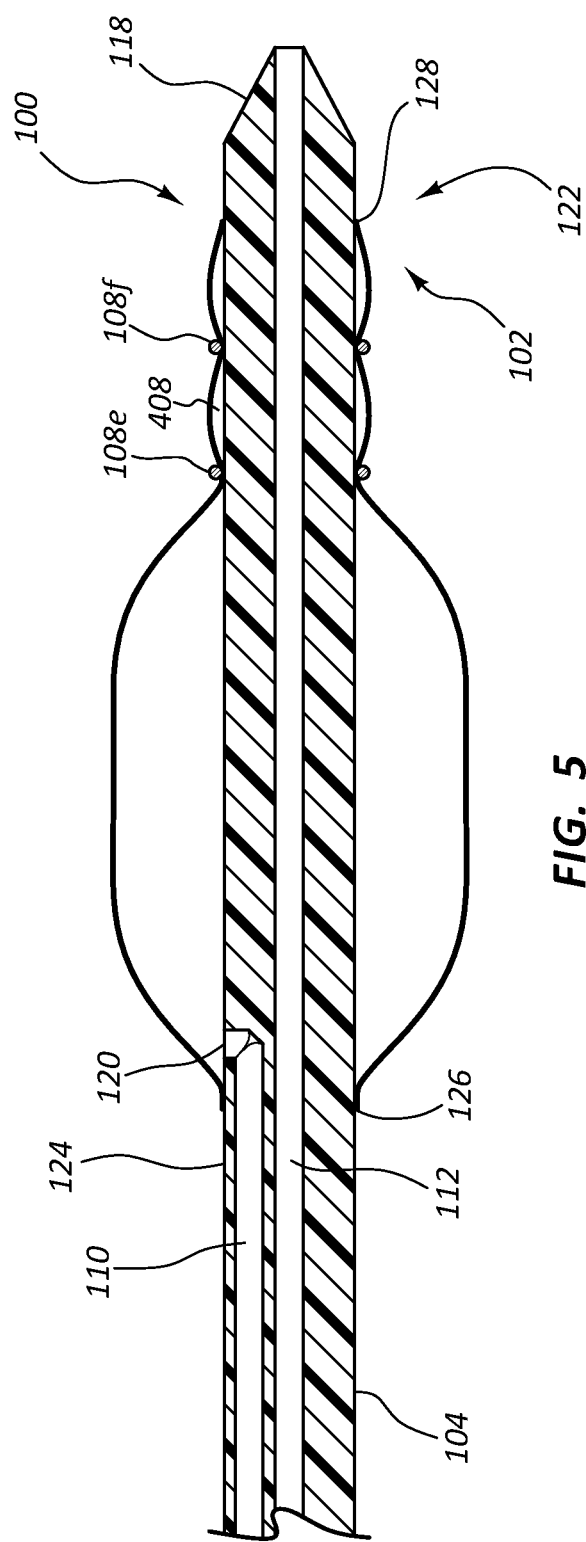
FIG. 5 illustrates the cross-sectional view of FIG. 2 with multiple balloon sections expanded.

FIG. 5 illustrates the variable length balloon 106 have 4 stricture mechanisms 108 ruptured. The variable length balloon 106 is now at the working length and may be used to carry out an angioplasty in the arterial wall. The working length of the variable length balloon 106 will not change as long as the rupture pressure of the fifth stricture mechanism 108e is not exceeded. In some embodiments the sizing of the balloon and the angioplasty may be carried out simultaneously. For example, the variable length balloon 106 may be present within the arterial wall while each stricture mechanism 108 is ruptured. In other embodiments, the balloon may be sized prior to the angioplasty. For example, the stricture mechanisms 108 may be ruptured before the balloon is inserted into the arterial wall. The balloon may then be deflated and passed into the arterial wall for the angioplasty procedure. This is advantageous in that the balloon will then inflate uniformly over the working length instead of in segments while it is being sized.

Returning to the previous example, the process of sizing the variable length balloon 106 will now be described. It will be assumed that the variable length balloon 106 is being sized to a working length of 10 cm, that the first stricture mechanism 108a has a rupture pressure of 15 psi, and that each additional rupture mechanism 108 has a rupture pressure increasing by 2.5 psi.

The operator will initially deliver inflation fluid to the first sub volume 300, which will gradually inflate the variable length balloon 106 and increase the fluid pressure within the first sub volume 300. When the fluid pressure in the first sub volume 300 exceeds 15 psi, the first stricture mechanism 108a will rupture and the inflation fluid will flow into the second sub volume 400. The inflation fluid continues to fill the combined first volume 300 and second volume 400 expanding the variable length balloon 106 and increasing the fluid pressure. When the fluid pressure exceeds 17.5 psi, the second stricture mechanism 108b will rupture and the inflation fluid will flow from the combined first volume 300 and second volume 400 and flow into a third sub volume 402. The inflation fluid continues to fill the combined first volume 300, second volume 400, and third volume 402 and inflate the variable length balloon 106. The fluid pressure increases until it exceeds 20 psi at which point the third stricture mechanism 8c ruptures. Fluid then flows between the combined first 300, second 400 and third sub volume 402, and the fourth sub volume 404. The inflation fluid continues to fill the combined first 300, second 400, third 402, and forth sub volumes 404 and inflate the variable length balloon 106. The fluid pressure increases until it exceeds 22.5 psi, at which point the fourth stricture mechanism 8d ruptures allowing inflation fluid to flow from the combined first 300, second 400, third 402 and fourth sub 404 volumes into the fifth sub volume 406. With inflation fluid flowing into all 5 sub volumes the variable length balloon 106 is now sized to the working length. As long as the inflation fluid is not pressurized above 25 psi, the variable length balloon 106 will maintain its working length. Because the rupture pressure of each stricture mechanism 108 is predetermined and the operator knows the rupture pressure of the fourth stricture mechanism 108d and the fifth rupture mechanism 108e, the operator can inflate the variable length balloon to a pressure between the pressure of the fourth stricture mechanism 108d and the fifth stricture mechanism 108e to obtain the working length of the variable length balloon.

In other embodiments, each of the stricture mechanisms 108 may have the same rupture pressure. For example, consider the previous example, but assume that each stricture mechanism 108 has a rupture pressure of 20 psi. The operator will initially deliver inflation fluid to the first sub volume 300, which will gradually inflate the variable length balloon 106 and increase the fluid pressure within the first sub volume 300. When the fluid pressure in the first sub volume exceeds 20 psi, the first stricture mechanism 108a will rupture and the inflation fluid will flow into the second sub volume 400. Because the combined volume of the first sub volume 300 and the second sub volume 400 is greater than the first volume 300 alone, the pressure in the combined volume will drop as the second volume 400 inflates. This drop in pressure may be observed, indicating that a stricture mechanism 108 has been ruptured. The inflation fluid continues to fill the combined first 300 and second volume 400 expanding the variable length balloon 106 and increasing the fluid pressure again. When the fluid pressure reaches 20 psi again, the second stricture mechanism 108b will rupture and the inflation fluid will flow from the combined first 300 and second volume 400 and flow into the third sub volume 402. Once again the fluid pressure drops as the third volume 402 begins to inflate. This pressure drop can be observed indicating a second stricture mechanism 108b has ruptured. The inflation fluid continues to fill the combined first 300, second 400, and third volume 402 and inflate the variable length balloon 106. The fluid pressure increases until it exceeds 20 psi again at which point the third stricture mechanism 108c ruptures. Fluid then flows between the combined first 300, second 400 and third sub volume 402, and the fourth sub volume 404 and another pressure drop is observed indicating the third stricture mechanism 108c has failed. The inflation fluid continues to fill the combined first 300, second 400, third 402, and forth sub volumes 404 and inflate the variable length balloon 106. The fluid pressure increases until it exceeds 20 psi again, at which point the fourth structure mechanism 108d ruptures allowing fluid to flow from the combined first 300, second 400, third 402 and fourth sub volumes 404 into the fifth sub volume 406. The fourth pressure drop is observed and the operator will recognize that the variable length balloon 106 is now sized to the working length. As long as the operator does not exceed 20 PSI again, the working length of the variable length balloon 106 will not change.

While the process for sizing the variable length balloon 106 has been described in terms of FIG. 2 which illustrates a suture stricture mechanism 108, it will be recognized that the method will be the same if other stricture mechanisms 108 are used. Additionally, while the variable length balloon and the method of sizing it have been described in relation to an angioplasty, they are suitable for use in other applications requiring a variable length balloon. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed:

1. A balloon catheter assembly comprising: a catheter having a distal end, a proximal end, and a lumen extending from the proximal end to the distal end;
   a variable length balloon disposed on the distal end of the catheter, the variable length balloon having an inner volume in fluid communication with the lumen and being defined by an outer surface of the catheter and an inner surface of a balloon wall; and
   a first pressure dependent stricture mechanism comprising a first band disposed about the variable length balloon, the first band constricting a first circumferential portion of the balloon wall proximate the outer surface of the catheter, the first pressure dependent stricture mechanism having a first pre-determined rupture pressure;
   a second pressure dependent stricture mechanism comprising a second band disposed about the variable length balloon, the second band constricting a second circumferential portion of the balloon wall proximate the outer surface of the catheter, the second pressure dependent stricture mechanism having a second pre-determined rupture pressure;
   a third pressure dependent stricture mechanism comprising a third band disposed about the variable length balloon, the third pressure dependent stricture mechanism constricting a third circumferential portion of the balloon wall proximate the outer surface of the catheter and a third pre-determined rupture pressure greater than the second predetermined rupture pressure; and
   whereby the first pressure dependent stricture mechanism and the second pressure dependent stricture mechanism divide the inner volume into longitudinal sections.

2. The balloon catheter assembly of claim 1 wherein the second pre-determined rupture pressure is greater than the first predetermined rupture pressure.

3. The balloon catheter assembly of claim 1 wherein the first pressure dependent stricture mechanism, the second pressure dependent stricture mechanism, and the third pressure dependent stricture mechanism divide the inner volume into longitudinal sections of equal length.

4. The balloon catheter assembly of claim 1 wherein the first band and second band are each comprised of a biodegradable material.

5. The balloon catheter assembly of claim 4 wherein the first stricture mechanism has a lower tensile strength than the second stricture mechanism.

6. The balloon catheter assembly of claim 1 wherein the first predetermined rupture pressure is 15 pounds per square inch.

7. The balloon catheter assembly of claim 1 wherein the second pre-determined rupture pressure is equal to the first pre-determined rupture pressure.

8. A method for varying the length of the variable length balloon of the balloon catheter assembly of claim 1, the method comprising:
   guiding the variable length balloon to an inflation location;
   determining a desired length to inflate the variable length balloon;
   determining a plurality of pressure dependent stricture mechanisms to rupture to achieve a working length near the desired length;
   for each of the plurality of pressure dependent stricture mechanisms, rupturing the pressure dependent stricture mechanism by introducing fluid into the inner volume of the balloon sufficient to exceed the rupture pressure threshold of at least one pressure dependent stricture mechanisms; and
   introducing fluid to expand the balloon at a pressure less than a predetermined rupture pressure threshold of a stricture mechanism not among the second plurality of stricture mechanisms.

9. The method of claim 8 wherein the working length is greater than the desired length.

10. The method of claim 8 wherein each of the pressure dependent stricture mechanisms have a rupture pressure threshold greater than a plurality of stricture mechanism located proximal to the stricture mechanism.

11. A method of manufacturing the balloon catheter assembly of claim 1 comprising:
   obtaining a catheter having at least one inflation lumen and an inflation port in fluid communication with the inflation lumen;
   placing a balloon material about an outer surface of the catheter at a distal end of the catheter;
   securing the balloon material in a circumferential strip to the outer surface of the catheter proximal to the inflation port;
   securing the balloon material in a circumferential strip to the outer surface of the catheter distal to the inflation port; and
   attaching a plurality of pressure dependent stricture mechanisms in circumferential strips about the catheter, the plurality of pressure dependent stricture mechanisms forming a pressure dependent attachment of the circumferential strip of the balloon material to the outer surface of the catheter.

12. The method of claim 11 wherein attaching a plurality of pressure dependent stricture mechanism comprises wrapping a suture about the balloon material.

13. The method of claim 11 wherein attaching a plurality of pressure dependent stricture mechanisms comprises providing a plurality of circumferential strips of adhesive between the balloon material and the outer surface of the catheter.

14. The method of claim 11 wherein the catheter has an inner layer and an outer layer, the inner laying having a melting point lower than the outer layer and wherein attaching a plurality of pressure dependent stricture mechanisms comprising heating the balloon material in a plurality of circumferential strips sufficient to cause the inner layer to bond to the outer surface of the catheter.

* * * * *